United States Patent [19]

Becker et al.

[11] 4,334,072
[45] Jun. 8, 1982

[54] LACTONE COMPOUNDS CONTAINING AN INDOLIZINE RADICAL

[75] Inventors: William J. Becker; Sheldon Farber; Troy E. Hoover, all of Appleton, Wis.

[73] Assignee: Appleton Papers Inc., Appleton, Wis.

[21] Appl. No.: 192,152

[22] Filed: Sep. 29, 1980

Related U.S. Application Data

[60] Division of Ser. No. 112,500, Jan. 16, 1980, Pat. No. 4,275,206, which is a continuation-in-part of Ser. No. 17,764, Mar. 5, 1979, Pat. No. 4,232,887.

[51] Int. Cl.³ .................. C07D 401/14; C07D 405/14
[52] U.S. Cl. ....................................................... 546/112
[58] Field of Search ........................................ 546/112

[56] References Cited

U.S. PATENT DOCUMENTS

| | | | |
|---|---|---|---|
| 3,509,173 | 4/1970 | Lin | 260/326.14 |
| 3,540,909 | 11/1970 | Lin | 117/36.2 |
| 3,936,564 | 2/1976 | Miyazawa et al. | 428/307 |
| 4,020,068 | 4/1977 | Farber | 260/250 Q |

Primary Examiner—John M. Ford
Attorney, Agent, or Firm—E. Frank McKinney; Paul S. Phillips, Jr.

[57] ABSTRACT

Chromogenic compounds of normally colorless form are disclosed having the following structural formula:

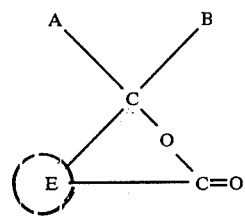

wherein E represents a six-membered aromatic or heterocyclic ring which may have an aromatic condensed ring or a naphthalene ring and both the E ring and the condensed ring may be substituted, A represents an optionally substituted aminophenyl, indolyl, benzoindolyl, julolidinyl or kairolyl radical or the radical represented by B, and B represents a family of indolizine radicals. The compounds of this invention are eligible for use in pressure-sensitive and heat-sensitive record materials and manifold marking systems.

20 Claims, No Drawings

LACTONE COMPOUNDS CONTAINING AN INDOLIZINE RADICAL

This application is a divisional of copending application Ser. No. 112,500, filed Jan. 16, 1980 and now U.S. Pat. No. 4,275,206, which is a continuation-in-part of copending application Ser. No. 17,764 filed Mar. 5, 1979 and now U.S. Pat. No. 4,232,887.

TECHNICAL FIELD

This invention pertains to novel chromogenic compounds which can give intense colors when they are contacted with an electron accepting co-reactant. More specifically, this invention relates to chromogenic compounds eligible for use in pressure-sensitive or heat-sensitive mark-forming record systems. Such systems are improved by use of these compounds. As used in mark-forming systems, marking in desired areas on support webs or sheets may be accomplished by effecting localized reactive contact between the chromogenic material and the electron accepting material on or in such a web or sheet, such material being brought thereto by transfer, or originally there in situ, the desired reactive contact forming colored images in the intended image-marking areas.

The chromogenic compounds of this invention have the following general formula:

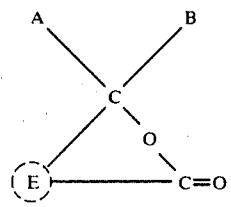

wherein E represents a benzene nucleus which is unsubstituted or substituted by one or more halogen, alkyl or dialkylamino groups, or, as a heterocyclic ring, E represents mainly a nitrogen containing heterocycle of aromatic character such as a pyridine or pyrazine ring. The ring E may also contain a condensed aromatic ring representing, for example, a naphthalene, quinoline or quinoxaline ring, which may be substituted by one or more halogen groups, A represents an optionally substituted aminophenyl, indolyl, benzoindolyl, julolidinyl or kairolyl radical, or the radical represented by B, B represents a family of indolizine radicals.

BACKGROUND ART

Several different types of chromogenic lactone compounds are described in U.S. patent reissue No. 23,024, U.S. Pat. Nos. 3,491,112, 3,491,116, 3,509,173, 3,540,909, 3,540,911, 3,540,912, 3,736,337, 3,775,424, 3,853,869 and 4,020,068 and in Belgian patent No. 844,962.

U.S. Pat. No. 3,958,815 describes carbinol ether compounds containing indolizinyl groups.

DISCLOSURE OF THE INVENTION

Colorable novel chromogenic lactone compounds having indolizine radicals have been discovered. These compounds are initially substantially colorless but produce colored products on reaction with certain acid materials. It is an object of this invention to provide compounds containing such indolizine radicals, methods for making them and mark-forming record systems containing them.

It is another object of this invention to provide indolizine-containing compounds which produce substantially the same color of mark with different types of acid reactants.

It is yet another object to provide such compounds which produce colored marks which are resistant to actinic radiation.

The compounds of this invention produce substantially more color on one or more types of acid reactant surfaces than do the carbinol ether compounds disclosed in the prior art.

Important groups of colorable chromogenic lactone compounds having these indolizine radicals may be defined by the formula:

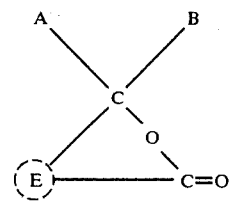

wherein E represents an optionally substituted benzene, pyridine, pyrazine, quinoline or quinoxaline ring, A represents an optionally substituted aminophenyl, indolyl, benzoindolyl, julolidinyl or kairolyl radical, and B represents a family of indolizine radicals hereinafter defined.

Among the more important compounds of this invention are the ones defined by the formula:

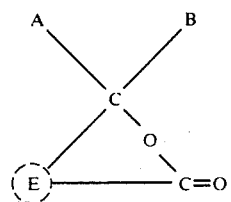

wherein E represents an optionally substituted benzene, pyridine, pyrazine, quinoline or quinoxaline ring, A represents an optionally substituted aminophenyl, indolyl, benzoindolyl, julolidinyl or kairolyl radical, and B represents an indolizine radical selected from:

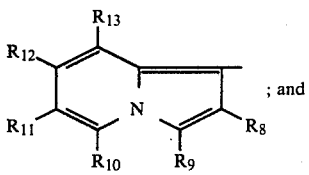 ; and

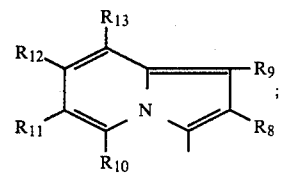 ;

wherein $R_8$ represents aryl, substituted aryl, pyridyl, and alkyl; $R_9$ represents hydrogen, alkyl, aryl and benzyl; $R_{10}$, $R_{11}$, $R_{12}$ and $R_{13}$ represent hydrogen, alkyl, halogen and nitro.

The more preferred among the compounds of this invention are the ones represented by the following formulas:

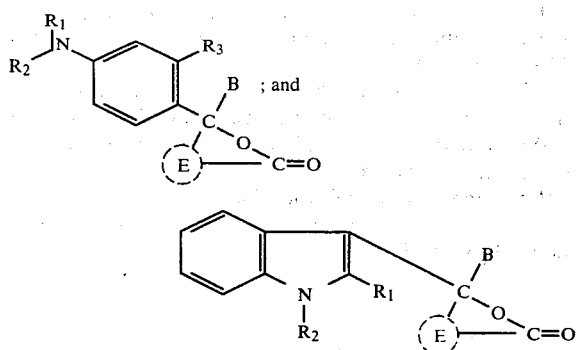

wherein E represents an optionally substituted benzene, pyridine, pyrazine, quinoline or quinoxaline ring, and B represents an indolizine radical selected from:

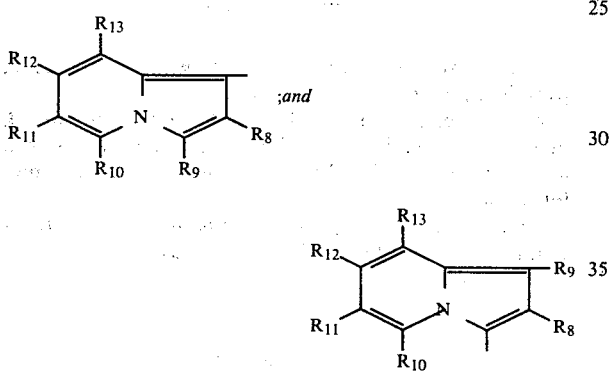

$R_1$ and $R_2$ represent hydrogen and alkyl, $R_3$ represents hydrogen and alkoxy, $R_8$ represents alkyl, pyridyl, aryl and substituted aryl, $R_9$ represents hydrogen, alkyl and aryl, $R_{10}$, $R_{11}$, $R_{12}$, and $R_{13}$ represent hydrogen, alkyl and nitro.

Most preferred among the compounds of this invention are those represented by the following formulas:

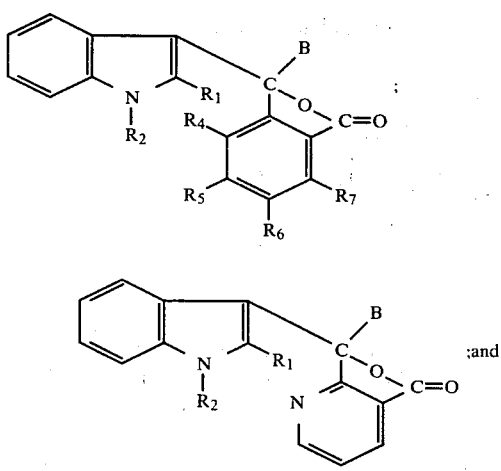

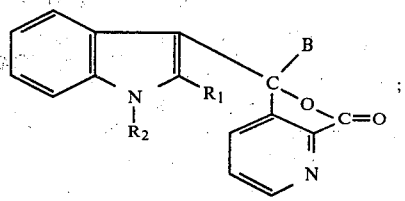

wherein B represents an indolizine radical selected from:

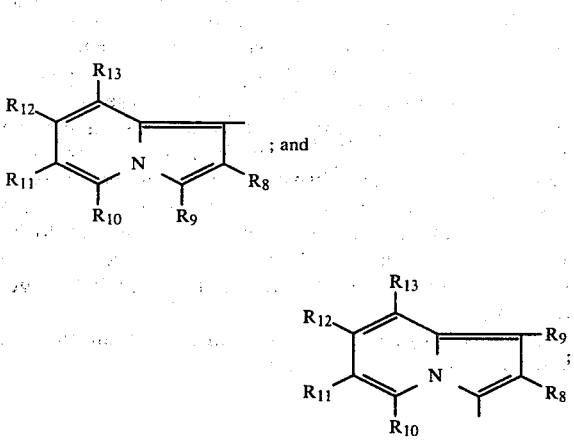

$R_1$ and $R_2$ represent hydrogen and alkyl, $R_4$, $R_5$, $R_6$ and $R_7$ represent hydrogen, chlorine and dialkylamino, $R_8$ represents aryl, substituted aryl, pyridyl and alkyl, $R_9$ represents hydrogen, alkyl, aryl and benzyl, $R_{10}$, $R_{11}$, $R_{12}$ and $R_{13}$ represent hydrogen, alkyl and nitro.

Alternatively important groups of colorable chromogenic lactone compounds having indolizine radicals may be defined by the formula:

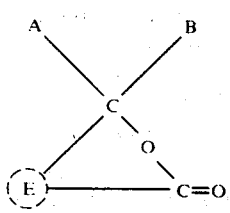

wherein E represents an optionally substituted benzene, pyridine, pyrazine, naphthalene, quinoline or quinoxaline ring, A represents an optionally substituted aminophenyl radical and B represents a family of indolizine radicals hereinafter defined.

Among the more important compounds of the alternative groups of this invention are the ones represented by the formula:

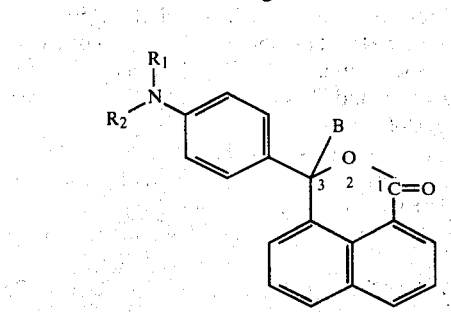

wherein B represents an indolizine radical selected from:

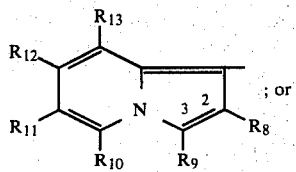

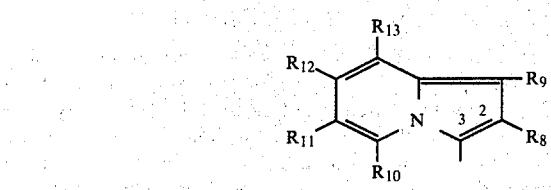

$R_1$ and $R_2$ represent hydrogen or alkyl,
$R_8$ represents phenyl, substituted phenyl or alkyl,
$R_9$ represents hydrogen, alkyl or phenyl,
$R_{10}$, $R_{11}$, $R_{12}$ and $R_{13}$ represent hydrogen or alkyl.

Other important groups of colorable chromogenic lactone compounds having indolizine radicals may be defined by the formula:

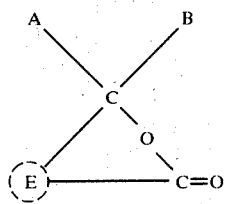

wherein E represents an optionally substituted benzene, pyridine, pyrazine, quinoline or quinoxaline ring,
A represents an optionally substituted aminophenyl, or indolyl radical or the radical represented by B, and B represents an indolizine radical hereinafter defined.

Among the more important compounds of the alternative group of the invention are the ones represented by the formula:

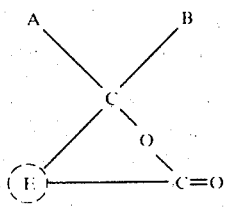

wherein E represents

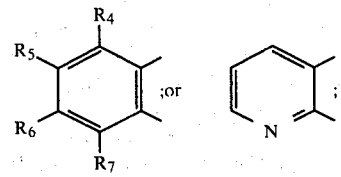

$R_4$, $R_5$, $R_6$ and $R_7$ represent hydrogen, chlorine or dialkylamino;
A represents

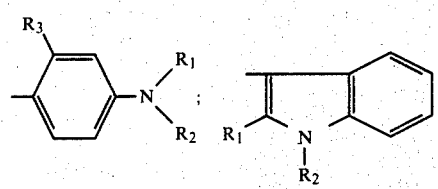

or B;
$R_1$ and $R_2$ represent hydrogen or alkyl;
$R_3$ represents hydrogen or alkoxy;
B represents

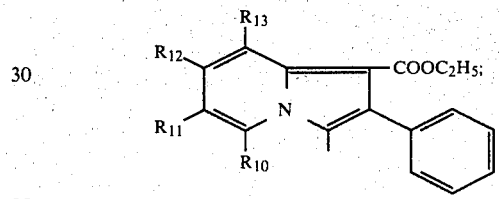

and $R_{10}$, $R_{11}$, $R_{12}$ and $R_{13}$ represent hydrogen or alkyl.

Advantageously, the lactone compounds according to this invention are manufactured by reacting a compound of the formula:

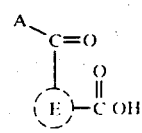

hereinafter called the keto acid, with an indolizine compound, hereinafter called substrate reactant B, wherein A, E, and B are as previously defined.

This reaction is desireably carried out by allowing the reactants to react together in the presence of an acidic dehydrating agent.

Best Mode for Carrying Out the Invention

The chromogenic compounds of this invention are eligible for use in pressure-sensitive and thermally-sensitive mark-forming systems. Pressure-sensitive mark-forming systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation preferably comprises microcapsules containing liquid solvent solution. The microencapsulation process utilized can be chosen from the many known in the art. Well known methods are disclosed in U.S. Pat. Nos. 2,800,457, 3,041,289, 3,533,958, 3,755,190, 4,001,140 and 4,100,103. Any of these and other methods are suitable for encapsulating the liquid solvent containing the chromogenic compounds of this invention.

The method of marking comprises providing a chromogenic compound of the present invention and bringing such chromogenic compound into reactive contact, in areas where marking is desired, with an acidic color-activating substance to produce a colored form of the chromogenic compound.

The acidic materials can be any compound within the definition of a Lewis acid, i.e. an electron acceptor. These materials include clay substances such as attapulgite, bentonite and montmorillonite and treated clays such as silton clay as disclosed in U.S. Pat. Nos. 3,622,364 and 3,753,761, materials such as silica gel, talc, feldspar, magnesium trisilicate, pyrophyllite, zinc sulfate, zinc sulfide, calcium sulfate, calcium citrate, calcium phosphate, calcium fluoride and barium sulfate, aromatic carboxylic acids such as salicylic acid, derivatives of aromatic carboxylic acids and metal salts thereof as disclosed in U.S. Pat. No. 4,022,936 and acidic polymeric material such as phenol-formaldehyde polymers, phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof as disclosed in U.S. Pat. No. 3,672,935.

Particularly useful as acid color-activating substances are the metal-modified phenolic resins. Record sheet material coated with such resins is disclosed in U.S. Pat. No. 3,732,120. An example of the compositions which can be coated onto the surface of a sheet to react with the chromogenic compounds of this invention is as follows:

| Coating Composition | Percent by Weight |
| --- | --- |
| Zinc-modified phenolic polymer | 13.6 |
| Paper coating kaolin | 67.9 |
| Calcium carbonate | 6.0 |
| Styrene-butadiene latex | 6.0 |
| Etherified corn starch | 6.5 |

The following examples are given merely as illustrative of the present invention and are not to be considered as limiting.

The intermediates required for the preparation of the novel chromogenic compounds of this invention are classes of compounds readily obtained by procedures well known in the prior art.

The intermediates, substrate reactant B, which result in the indolizine radical portion of the novel chromogenic compounds can be made by procedures analogous to those in one or more of the following references:

1. T. Uchida and K. Matsumoto, Synthesis, 209(1976) and references therein.
2. N. P. Buu-Hoi et. al., J. Org. Chem. 19, 1370(1954).
3. J. Fisher and J. Straley, British Pat. 1,159,691.
4. N. P. Buu-Hoi, Nguyen-Dat-Xuong and Ta-Thu-Cuc, Bull. Soc. Chim. France, 1277 (1966).
5. R. M. Palei and P. M. Kochergin, Khim. Geterotsikl. Soed. 536(1967)
6. F. Kroehnke and W. Zecher, Ber. 95, 1128(1962).
7. A. Druyhinina, P. Kochergin and N. Bychkove, Khim. Geterotshikl Soed., 856(1969).
8. F. Kroehnke and W. Friedrich, Ber. 96, 1195(1963).
9. G. W. H. Cheeseman and B. Tuck, J. Chem. Soc. 3678(1965).

The other reactant, the keto acid, required for the preparation of the novel chromogenic compounds of this invention is disclosed in U.S. Pat. Nos. 3,491,111, 3,491,112, 3,491,116, 3,509,173, 3,775,424, 3,936,564, 4,020,068 and 4,022,771 and in Belgian Pat. No. 844,962.

Unless otherwise noted, the percentages throughout the application are by weight.

EXAMPLE 1

Preparation of 3-(1-ethyl-2-methylindol-3-yl)-3-(1-methyl-2-naphthylindolizin-3-yl)phthalide A mixture of 3.0 grams of (1-ethyl-2-methylindol-3-yl) (2-carboxyphenyl)ketone, 2.5 grams of 1-methyl-2-(2-naphthyl) indolizine and 10 ml. of acetic anhydride was heated at 39° C. for about two hours. The resulting solution was cooled and added to a mixture of ice, toluene and ammonia. The toluene layer was separated, dried, treated with charcoal and filtered. Petroleum ether was added and after fractional precipitation a crystalline product was obtained and recrystallized from a toluene-heptane mixture to a constant melting point of 191°–193° C. A chloroform solution of this final product gave a blue color when applied to a record sheet material coated with a zinc-modified phenolic resin.

EXAMPLE 2

Preparation of 3-(1-ethyl-2-methylindol-3-yl)-3-(1,2-diphenylindolizin-3-yl)phthalide A mixture of 3.06 grams of (1-ethyl-2-methylindol-3-yl) (2-carboxyphenyl)ketone, 2.7 grams of 2,3-diphenylindolizine and 10 ml. of acetic anhydride was heated at about 50° C. for 107 minutes. The reaction mixture was cooled and filtered and the obtained product was recrystallized from a toluene-heptane mixture. The 3.3 grams of product were recrystallized from a toluene-heptane mixture to a constant melting point of 227°–227.5° C. A chloroform solution of the product when applied to silica gel produced a blue color.

EXAMPLE 3

Preparation of 3-(1-ethyl-2-methylindol-3-yl)-3-(2,3-dimethylindolizin-1-yl)-4,5,6,7-tetrachlorophthalide A mixture of 4.3 grams of (1-ethyl-2-methylindol-3-yl) (2-carboxy-3,4,5,6-tetrachlorophenyl)ketone, 1.5 grams of 2,3-dimethylindolizine and 10 ml. of acetic anhydride was heated at 90° C. for about seven and one-half hours. The reaction mixture was cooled and filtered and the filtrate was extracted with toluene. The toluene extract was washed with cold dilute ammonia, concentrated and filtered. The 0.9 gram of material obtained was recrystallized from a toluene-heptane mixture to yield a product with a melting point of 227.5°-228° C. A solution of this material in chloroform yielded a purple color when applied to a record sheet material coated with a zinc-modified phenolic resin.

EXAMPLES 4-11

According to substantially the same procedures as described in any one of the Examples 1 to 3, an indolizine compound of the formula

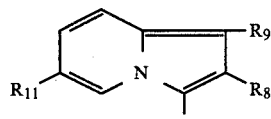

was mixed with an equimolar amount of (1-ethyl-2-methylindol-3-yl) (2-carboxyphenyl)ketone and about four to five grams of acetic anhydride were added per gram of reactant mixture. The reaction mixture was heated to 50°-60° C., poured over ice and adjusted to about pH 10 by the addition of ammonium hydroxide. The solid product was filtered and dried. A solution of the product in benzene or acetone was passed through a column of activated alumina to remove impurities. The solution was concentrated, the chromogenic material crystallized by the addition of heptane and the solid product was filtered and dried. In Table I are listed, respectively, the substituents on the indolizine reactant, the melting point and the color produced on silica gel by the resulting chromogenic compound product.

methyl-6-ethylindolizine and 10 ml of acetic anhydride was heated at 50° C. for about 30 minutes, the reaction product was poured into an ice-toluene mixture and the mixture was extracted with toluene. The toluene extract was passed through phase separation paper, concentrated on a steam bath, diluted with petroleum ether and filtered, yielding 1.7 grams of product. This material was recrystallized to a constant melting point of 223°-224° C. and a chloroform solution of the product gave a purple color when applied on a record sheet material coated with a zinc-modified phenolic resin or with silton clay.

EXAMPLE 13

Preparation of 3-(1-ethyl-2-methylindol-3-yl)-3-(2-phenyl-3-methyl-6-ethylindolizin-1-yl)-4-nitrophthalide A mixture of 1.7 grams of (1-ethyl-2-methylindol-3-yl) (2-carboxy-6-nitrophenyl)ketone, 1.2 grams of 2-phenyl-3-methyl-6-ethylindolizine and 10 ml. of acetic anhydride was heated to 52° C. for about 30 minutes. The reaction mixture was poured into a mixture of ice, toluene and ammonia. The toluene layer was separated and evaporated to dryness yielding 1.0 grams of oily product which was chromatographed on diatomaceous earth. Two fractions were obtained from the chromatography. One portion of 40 mg. had a melting point of 254° C. and the other portion of 10 mg. had a melting point of 225° C. Solutions of both produced purple colors on silica gel.

Additional experiments were performed where a keto acid and a substrate reactant B were mixed with acetic

TABLE I

| | Indolizine Substituents | | | Melting Point | | Color on |
| --- | --- | --- | --- | --- | --- | --- |
| Example | R₈ | R₉ | R₁₁ | Darkens or Softens | Decomposition | Silica Gel |
| 4. | —⟨phenyl⟩ | —CH₃ | H | 208° C. | 212-216° C. | Blue |
| 5. | —⟨phenyl⟩ | H | H | 196° C. | 208-212° C. | Blue |
| 6. | —⟨phenyl⟩ | H | —C₂H₅ | 145° C. | 200-205° C. | Blue |
| 7. | —⟨phenyl⟩—OCH₃ | H | —C₂H₅ | 138° C. | 145-150° C. | Blue |
| 8. | —⟨phenyl⟩—⟨phenyl⟩ | H | H | 165° C. | 171-175° C. | Blue |
| 9. | —⟨phenyl⟩—OCH₃ | CH₃ | H | 170° C. | 145-150° C. | Blue |
| 10. | —⟨phenyl⟩—OCH₃ | H | H | 115° C. | 165-170° C. | Blue |
| 11. | —⟨phenyl⟩—Cl | H | H | 150° C. | 174-178° C. | Blue |

EXAMPLE 12

Preparation of 3-(1-ethyl-2-methylindol-3-yl)-3-(2-phenyl-3-methyl-6-ethylindolizin-1-yl)phthalide A mixture of 1.5 grams of (1-ethyl-2-methylindol-3-yl) (2-carboxyphenyl)ketone, 1.2 grams of 2-phenyl-3- anhydride and heated. The reaction mixture was cooled, treated with dilute ammonium hydroxide and extracted with toluene. In Table II is a listing of the reactant pairs and the respective color produced when the toluene extract of the reaction product was applied to a record sheet material coated with a zinc-modified phenolic resin.

TABLE II

| Keto Acid | Substrate Reactant B | Color Produced |
|---|---|---|
| (1-ethyl-2-methylindol-3-yl)(2-carboxyphenyl)ketone | 2-methylindolizine | Purple |
| (1-ethyl-2-methylindol-3-yl)(2-carboxyphenyl)ketone | 2-phenyl-3-methylindolizine | Purple |
| (1-ethyl-2-methylindol-3-yl)(2-carboxyphenyl)ketone | 1,2-dimethylindolizine | Purple |
| (1-ethyl-2-methylindol-3-yl)(2-carboxyphenyl)ketone | 2-phenyl-5-methylindolizine | Purple |
| (1-ethyl-2-methylindol-3-yl)(2-carboxyphenyl)ketone | 2-(2-pyridyl)indolizine | Blue |
| (1-ethyl-2-methylindol-3-yl)(2-carboxy-3,4,5,6-tetrachlorophenyl)ketone | 2-methylindolizine | Blue |
| (1-ethyl-2-methylindol-3-yl)(2-carboxy-3,4,5,6-tetrachlorophenyl)ketone | 2-phenylindolizine | Blue |
| (1-ethyl-2-methylindol-3-yl)(2-carboxy-3,4,5,6-tetrachlorophenyl)ketone | 1-methyl-2-phenylindolizine | Blue |
| (1-ethyl-2-methylindol-3-yl)(2-carboxy-3,4,5,6-tetrachlorophenyl)ketone | 2-phenyl-3-methylindolizine | Blue |
| (1-ethyl-2-methylindol-3-yl)(2-carboxy-3,4,5,6-tetrachlorophenyl)ketone | 1-methyl-2-naphthylindolizine | Blue |
| (1-ethyl-2-methylindol-3-yl)(2-carboxy-3,4,5,6-tetrachlorophenyl)ketone | 1,2-diphenylindolizine | Green |
| (1-ethyl-2-methylindol-3-yl)(2-carboxy-3,4,5,6-tetrachlorophenyl)ketone | 1,2-dimethylindolizine | Red |
| (1,2-dimethylindol-3-yl)(2-carboxy-3-nitrophenyl)ketone | 2-phenyl indolizine | Blue |
| (1,2-dimethylindol-3-yl)(2-carboxy-3-nitrophenyl)ketone | 2-phenyl-5-methylindolizine | Purple |
| (1-methyl-2-phenylindol-3-yl)(2-carboxy-3-nitrophenyl)ketone | 1-methyl-2-phenylindolizine | Blue |
| (1-methyl-2-phenylindol-3-yl)(2-carboxy-3-nitrophenyl)ketone | 1-methyl-2-naphthylindolizine | Blue |
| (1-methyl-2-phenylindol-3-yl)(2-carboxy-3-nitrophenyl)ketone | 1,2-diphenylindolizine | Green |
| (1-methyl-2-phenylindol-3-yl)(2-carboxy-3-nitrophenyl)ketone | 1,2-dimethylindolizine | Blue |
| (1-methyl-2-phenylindol-3-yl)(2-carboxy-3-nitrophenyl)ketone | 2-phenyl-5-methylindolizine | Green |

EXAMPLE 14

Preparation of 3-(4-diethylamino-2-methoxyphenyl)-3-(2,3-dimethylindolizin-1yl)phthalide A mixture of 3.3 grams of 2-methoxy-4-diethylamino-2-carboxybenzophenone, 1.5 grams of 2,3-dimethylindolizine and 10 ml. of acetic anhydride was heated at 40° C. for about one hour and then cooled in an ice bath. The resulting crystalline material was separated by filtration and recrystallized from heptane to yield 1.2 grams of product. This material was recrystallized three more times to yield a product with a constant melting point of 192.5°–193.5° C. A chloroform solution of the final product produced a blue color when applied to a record sheet material coated with a zinc-modified phenolic resin.

EXAMPLES 15–18

According to substantially the same procedure as described in Example 14, a keto acid was reacted with a substantially equimolar amount of a substrate reactant B in the presence of acetic anhydride with heating. The solid product was separated and recrystallized to a constant melting point. A solution of this product in chloroform was used to produce a color on a record sheet material coated with a zinc-modified phenolic resin or silton clay or on silica gel. These reactants and the results obtained are listed in Table III.

TABLE III

| Example | Keto Acid | Substrate Reactant B | Yield | Melting Color | Color | Acid Reactant |
|---|---|---|---|---|---|---|
| 15 | 2-carboxy-4,4'-bis(dimethylamino)benzophenone | 1-methyl-2-phenyl-indolizine | 44% | 171–172° C. | Blue | zinc-modified phenolic resin |
| 16 | 2-methoxy-4-diethylamino-2'-carboxybenzophenone | 1-methyl-2-phenyl-indolizine | 37% | 206–208° C. | Blue | zinc-modified phenolic resin |
| 17 | 2-ethoxy-4-diethylamino-2'-carboxybenzophenone | 2-(2,5-dimethoxyphenyl)-indolizine | 95% | 95–98° C. | Green | silton clay |
| 18 | 2-carboxy-4,4'-bis(dimethylamino)benzophenone | 2-phenyl-3-methyl-6-ethylindolizine | | 226–228° C. | Purple | silica gel |
| 19 | 2-carboxy-4,4'-bis(dimethylamino)benzophenone | 2-phenyl-3-methyl-indolizine | 16% | 193–194° C. | Blue | zinc-modified phenolic resin |
| 20 | 2-carboxy-4,4'-bis(dimethylamino)benzophenone | 1-methyl-2-(2-naphthyl)-indolizine | 89% | 217–220° C. | Blue | zinc-modified phenolic resin |
| 21 | 2-carboxy-4,4'-bis(dimethylamino)benzophenone | 2-(2-pyridyl)-indolizine | 61% | 196.5–197.0° C. | Blue-Green | zinc-modified phenolic resin |
| 22 | 2-carboxy-4,4'-bis(dimethylamino)benzophenone | 1-phenyl-2-(2-pyridyl)-indolizine | 5% | 245–246° C. | Blue-Green | zinc-modified phenolic resin |

Additional experiments were performed where a keto acid and a substrate reactant B were mixed with acetic anhydride and heated. The reaction mixture was cooled, treated with dilute ammonium hydroxide and extracted with toluene. In Table IV is a listing of the reactant pairs and the respective color produced when the toluene extract of the reaction product was applied to a record sheet material coated with a zinc-modified phenolic resin.

TABLE IV

| Keto Acid | Substrate Reactant B | Color Produced |
|---|---|---|
| 4'-diethylamino-2-carboxybenzophenone | 2-methylindolizine | Blue-Green |
| 4'-diethylamino-2-carboxybenzophenone | 2-phenylindolizine | Blue |
| 4'-diethylamino-2-carboxybenzophenone | 1-methyl-2-phenylindolizine | Blue-Green |
| 4'-diethylamino-2-carboxybenzophenone | 2-phenyl-3-methylindolizine | Blue |
| 4'-diethylamino-2-carboxybenzophenone | 1,2-diphenylindolizine | Green |
| 4'-diethylamino-2-carboxybenzophenone | 2-phenyl-3-methyl-6-ethylindolizine | Blue |
| 4'diethylamino-2-carboxybenzophenone | 2-phenyl-5-methylindolizine | Blue-Green |
| 4'-diethylamino-2-carboxy-3,4,5,6-tetrachlorobenzophenone | 2-methylindolizine | Green |
| 4'-diethylamino-2-carboxy-3,4,5,6-tetrachlorobenzophenone | 2-phenylindolizine | Green |
| 4'-diethylamino-2-carboxy-3,4,5,6-tetrachlorobenzophenone | 1-methyl-2-phenylindolizine | Green |
| 4'-diethylamino-2-carboxy-3,4,5,6-tetrachlorobenzophenone | 2-phenyl-3-methylindolizine | Green |
| 4'-diethylamino-2-carboxy-3,4,5,6-tetrachlorobenzophenone | 1,2-diphenylindolizine | Green |
| 4'-diethylamino-2-carboxy-3,4,5,6-tetrachlorobenzophenone | 2-phenyl-3-methyl-6-ethylindolizine | Green |
| 4'-diethylamino-2-carboxy-3,4,5,6-tetrachlorobenzophenone | 2-phenyl-5-methylindolizine | Green |
| 2-carboxy-4,4'-bis(dimethylamino)benzophenone | 2-methylindolizine | Blue |
| 2-carboxy-4,4'-bis(dimethylamino)benzophenone | 2-phenylindolizine | Blue |
| 2-carboxy-4,4'-bis(dimethylamino)benzophenone | 2-phenyl-3-methylindolizine | Purple |
| 2-carboxy-4,4'-bis(dimethylamino)benzophenone | 1,2-diphenylindolizine | Blue |
| 2-carboxy-4,4'-bis(dimethylamino)benzophenone | 2-phenyl-3-methyl-6-ethylindolizine | Purple |
| 2-carboxy-4,4'-bis(dimethylamino)benzophenone | 2-phenyl-5-methylindolizine | Purple |
| 2-carboxy-4,4'bis(dimethylamino)benzophenone | 2-methyl-3-phenylindolizine | Blue |
| 2-carboxy-4,4'-bis(dimethylamino)benzophenone | 2-(2-pyridyl)indolizine | Blue |
| 2-carboxy-2'-methoxy-4'-methyl-N-p-tolylaminobenzophenone | 2-methylindolizine | Blue |
| 2-carboxy-2'-methoxy-4'-methyl-N-p-tolylaminobenzophenone | 2-phenylindolizine | Blue |
| 2-carboxy-2'-methoxy-4'-methyl-N-p-tolylaminobenzophenone | 1-methyl-2-phenylindolizine | Blue-Green |
| 2-carboxy-2'-methoxy-4'-methyl-N-p-tolylaminobenzophenone | 2-phenyl-3-methylindolizine | Blue |
| 2-carboxy-2'-methoxy-4'-methyl-N-p-tolylaminobenzophenone | 1,2-diphenylindolizine | Green |
| 2-carboxy-2'-methoxy-4'-methyl-N-p-tolylaminobenzophenone | 2-phenyl-5-methylindolizine | Blue |
| 2-carboxy-3,4,5,6-tetrachloro-2'-methoxy-4'-diethylaminobenzophenone | 2-methylindolizine | Green |
| 2-carboxy-3,4,5,6-tetrachloro-2'-methoxy-4'-diethylaminobenzophenone | 2-phenylindolizine | Green |
| 2-carboxy-3,4,5,6-tetrachloro-2'-methoxy-4'-diethylaminobenzophenone | 1-methyl-2-phenylindolizine | Green |
| 2-carboxy-3,4,5,6-tetrachloro-2'-methoxy-4'-diethylaminobenzophenone | 2-phenyl-3-methylindolizine | Green |
| 2-carboxy-3,4,5,6-tetrachloro-2'-methoxy-4'-diethylaminobenzophenone | 1,2-diphenylindolizine | Green |
| 2-carboxy-3,4,5,6-tetrachloro-2'-methoxy-4'-diethylaminobenzophenone | 2-phenyl-3-methyl-6-ethylindolizine | Green |
| 2-carboxy-3,4,5,6-tetrachloro-2'-methoxy-4' diethylaminobenzophenone | 2-phenyl-5-methylindolizine | Green |
| 2-carboxy-2'-methoxy-4'-cyclohexylaminobenzophenone | 2-methylindolizine | Blue-Green |
| 2-carboxy-2'-methoxy-4'-cyclohexylaminobenzophenone | 2-phenyl-3-methylindolizine | Blue |
| 2-carboxy-2'-methoxy-4'-cyclohexylaminobenzophenone | 1,2-diphenylindolizine | Green |
| 2-carboxy-2'-methoxy-4'-cyclohexylaminobenzophenone | 2-phenyl-3-methyl-6-ethylindolizine | Green |
| 2-carboxy-2'-methoxy-4'-cyclohexylaminobenzophenone | 2-phenyl-5-methylindolizine | Blue |
| 2-carboxy-2'-n-butoxy-4'diethylaminobenzophenone | 1-methyl-2-phenylindolizine | Green |
| 2-carboxy-2'-n-butoxy-4'-diethylaminobenzophenone | 2-phenyl-3-methylindolizine | Blue |
| 2-carboxy-2'-n-butoxy-4'diethylaminobenzophenone | 1,2-diphenylindolizine | Green |
| 2-carboxy-2'-n-butoxy-'-diethylaminobenzophenone | 2-phenyl-3-methyl-6-ethylindolizine | Blue |
| 2-carboxy-2'-n-butoxy-4'-diethylaminobenzophenone | 2-phenyl-5-methylindolizine | Green |
| 2-carboxy-4'-morpholinobenzophenone | 1-methyl-2-phenylindolizine | Blue |
| 2-carboxy-4'-morpholinobenzophenone | 2-phenyl-3-methylindolizine | Blue |
| 2-carboxy-4'-morpholinobenzophenone | 1,2-diphenylindolizine | Blue |
| 2-carboxy-4'-morpholinobenzophenone | 2-phenyl-3-methyl-6-ethylindolizine | Blue |
| 2-carboxy-4'-morpholinobenzophenone | 2-phenyl-5-methylindolizine | Blue |

TABLE IV-continued

| Keto Acid | Substrate Reactant B | Color Produced |
| --- | --- | --- |
| 2-carboxy-2'-methoxy-4'-diethylaminobenzophenone | 2-methylindolizine | Blue-Green |
| 2-carboxy-2'-methoxy-4'-diethylaminobenzophenone | 2-phenylindolizine | Green |
| 2-carboxy-2'-methoxy-4'-diethylaminobenzophenone | 2-phenyl-3-methylindolizine | Blue |
| 2-carboxy-2'-methoxy-4'-diethylaminobenzophenone | 1,2-diphenylindolizine | Green |
| 2-carboxy-2'-methoxy-4'-diethylaminobenzophenone | 2-phenyl-3-methyl-6-ethylindolizine | Blue |
| 2-carboxy-2'-methoxy-4'-diethylaminobenzophenone | 2-phenyl-5-methylindolizine | Blue-Green |
| 2-carboxy-2'-methoxy-4'-diethylaminobenzophenone | 2-methyl-3-phenylindolizine | Green |
| 2-carboxy-2'-methoxy-4'-dimethylaminobenzophenone | 2-(2-pyridyl)indolizine | Green |

In the examples to follow which disclose the preparation of chromogenic compounds of the pyridinone and quinolinone types from the respective pyridinyl and quinolinyl keto acids, each reaction results in a mixture of two position isomers. Unless specifically stated, when the name of one isomer for either the keto acid or the chromogenic compound is given, a mixture of both isomers is understood. For example, the keto acid (1-ethyl-2-methylindol-3-yl) (3-carboxypyridin-2-yl)ketone in Example 19 is really a mixture of the named compound and its isomer, (1-ethyl-2-methylindol-3-yl) (2-carboxy-pyridin-3-yl) ketone. Likewise, the chromogenic compound product in Example 19, 7-(1-ethyl-2-methylindol-3-yl)-7-(1,2-diphenylindolizin-3-yl)-5,7-dihydrofuran[3,4-b]pyridin-5-one is actually a mixture of the named compound and its isomer, 5-(1-ethyl-2-methylindol-3-yl)-5-(1,2-diphenylindolizin-3-yl)-5,7-dihydrofuro[3,4-b]pyridin-7-one.

EXAMPLE 23

Preparation of
7-(1-ethyl-2-methylindol-3-yl)-7-(1,2-diphenylindolizin-3-yl)-5,7-dihydrofuro[3,4-b]pyridin-5-one A mixture of 1.6 grams of (1-ethyl-2-methylindol-3-yl) (3-carboxypyridin-2-yl)ketone, 1.85 grams of 1,2-diphenylindolizine and 10 ml. of acetic anhydride was heated at about 40° C. for 104 minutes and then cooled in an ice bath. The reaction mixture was filtered and the product was repeatedly recrystallized from a toluene-petroleum ether mixture until a constant melting point of 206.5°-207.5° C. was obtained. A chloroform solution of the final product produced a blue color when applied to a record sheet material coated with a zinc-modified phenolic resin.

EXAMPLES 24-28

According to substantially the same procedure as described in Example 23, (1-ethyl-2-methylindol-3-yl) (3-carboxypyridin-2-yl)ketone was reacted with a substantially equimolar amount of substrate reactant B in the presence of acetic anhydride with heating. The reaction product was separated and recrystallized to a constant melting point. A solution of each product was used to produce a color on record sheet material coated with a zinc-modified phenolic resin. These reactants and the results obtained are listed in Table V.

TABLE V

| Example | Substrate Reactant B | Yield | Melting Point | Color on zinc-modified phenolic resin record sheet |
| --- | --- | --- | --- | --- |
| 24 | 2,3-dimethylindolizine | 69% | 218-219° C. | Blue |
| 25 | 2-phenylindolizine | 33% | 200-201° C. | Blue |
| 26 | 2-(p-dimethylaminophenyl)indolizine | 37% | | Blue |
| 27 | 2-phenyl-3-methylindolizine | | 226-227.5° C. | Blue |
| 28 | 2-phenyl-3-methyl-6-ethylindolizine | | | Purple |

Additional experiments were performed where a keto acid and a substrate reactant B were mixed with acetic anhydride and heated. The reaction mixture was cooled, treated with dilute ammonium hydroxide and extracted with toluene. In Table VI is a listing of the reactant pairs and the respective color produced when the toluene extract of the reaction product was applied to a record sheet material coated with zinc-modified phenolic resin.

TABLE VI

| Keto Acid | Substrate Reactant B | Color Produced |
| --- | --- | --- |
| (1-ethyl-2-methylindol-3-yl)(3-carboxypyridin-2-yl)-ketone | 2-methylindolizine | Purple |
| (1-ethyl-2-methylindol-3-yl)(3-carboxypyridin-2-yl)-ketone | 1-methyl-2-phenylindolizine | Blue |
| (1-ethyl-2-methylindol-3-yl)(3-carboxypyridin-2-yl)-ketone | 2-phenyl-3-methylindolizine | Blue |
| (1-ethyl-2-methylindol-3-yl)(3-carboxypyridin-2-yl)-ketone | 1-methyl-2-naphthylindolizine | Blue |
| (1-ethyl-2-methylindol-3-yl)(3-carboxypyridin-2-yl)-ketone | 1,2-dimethylindolizine | Purple |
| (1-ethyl-2-methylindol-3-yl)(3-carboxypyridin-2-yl)-ketone | 2-phenyl-5-methylindolizine | Blue |
| (1-ethyl-2-methylindol-3-yl)(3-carboxypyridin-2-yl)-ketone | 2-methyl-3-phenylindolizine | Purple |
| (1-ethyl-2-methylindol-3-yl)(3-carboxypyridin-2-yl)-ketone | 2-(2-pyridyl)indolizine | Blue |

TABLE VI-continued

| Keto Acid | Substrate Reactant B | Color Produced |
|---|---|---|
| (1,2-dimethylindol-3-yl)(3-carboxypyridin-4-yl)ketone | 2-methylindolizine | Purple |
| (1,2-dimethylindol-3-yl)(3-carboxypyridin-4-yl)ketone | 2-phenyl-3-methylindolizine | Purple |
| (1,2-dimethylindol-3-yl)(3-carboxypyridin-4-yl)ketone | 1,2-diphenylindolizine | Purple |
| (1,2-dimethylindol-3-yl)(3-carboxypyridin-4-yl)ketone | 1,2-dimethylindolizine | Red |
| (1-isopentyl-2-methylindol-3-yl)(3-carboxypyridin-2-yl)ketone | 1-methyl-2-phenylindolizine | Blue |
| (1-isopentyl-2-methylindol-3-yl)(3-carboxypyridin-2-yl)ketone | 1-methyl-2-naphthylindolizine | Blue |
| (1-isopentyl-2-methylindol-3-yl)(3-carboxypyridin-2-yl)ketone | 1,2-diphenylindolizine | Blue-Green |
| (1-isopentyl-2-methylindol-3-yl)(3-carboxypyridin-2-yl)ketone | 1,2-dimethylindolizine | Purple |
| (1-isopentyl-2-methylindol-3-yl)(3-carboxypyridin-2-yl)ketone | 2-phenyl-5-methylindolizine | Blue |

EXAMPLE 29

Preparation of 5-(4-diethylamino-2-ethoxyphenyl)-5-(2-(2,5-dimethoxyphenyl)indolizin-3-yl)-5,7-dihydrofuro[3,4-b]pyridin-7-one A solution of 0.50 grams of 2-(2,5-dimethoxyphenyl)indolizine and 0.68 grams of (4-diethylamino-2-ethoxyphenyl)(3-carboxypyridin-2-yl)ketone in 15 ml. of acetic anhydride was heated 2 hours at 50° C. The solution was poured into 150 ml. of water, adjusted to pH 9.8 with ammonium hydroxide and stirred one hour. A benzene extraction was made. Evaporation of the dried benzene extract under reduced pressure left 1.13 grams of product. The infrared spectrum showed a strong lactone carbonyl peak at 1775 cm$^{-1}$. Thin layer chromatography showed a predominant green spot and a smaller bluish spot. A chloroform solution of the product produced a green color on a record sheet material coated with a zinc-modified phenolic resin or with silton clay.

EXAMPLES 30-35

According to substantially the same procedure as disclosed in Example 29, (4-diethylamino-2-ethoxyphenyl)(3-carboxypyridin-2-yl) ketone was reacted with a substantially equimolar amount of substrate reactant B in the presence of acetic anhydride and with heating. The reaction product was isolated and a chloroform solution of each product was used to produce a color on record sheet material coated with a zinc-modified phenolic resin. The results are listed in Table VII.

TABLE VII

| Example | Substrate Reactant B | Infrared Spectrum Peak | Melting Point | Color on zinc-modified phenolic resin record sheet |
|---|---|---|---|---|
| 30 | 5-methyl-2-(2,5-dimethoxyphenyl)indolizine | 1755 cm$^{-1}$ | 122-124° C. | Blue |
| 31 | 2-(p-dimethylaminophenyl)indolizine | 1765 cm$^{-1}$ | | Green |
| 32 | 2-phenyl-3-methyl-6-ethylindolizine | | | Blue-Green |
| 33 | 2-phenylindolizine | | | Green |
| 34 | 2-phenyl-3-methylindolizine | | | Green |
| 35 | 1-methyl-2-phenylindolizine | | | |

Additional experiments were performed where a keto acid and a substrate reactant B were mixed with acetic anhydride and heated. The reaction mixture was cooled, treated with dilute ammonium hydroxide and extracted with toluene. In Table VIII is a listing of the reactant pairs and the respective color produced when the toluene extract of the reaction product was applied to a record sheet material coated with a zinc-modified phenolic resin.

TABLE VIII

| Keto Acid | Substrate Reactant B | Color Produced |
|---|---|---|
| (4-diethylamino-2-ethoxyphenyl)(3-carboxypyridin-2-yl)ketone | 1,2-diphenylindolizine | Green |
| (4-diethylamino-2-ethoxyphenyl)(3-carboxypyridin-2-yl)ketone | 2,3-dimethylindolizine | Blue |
| (4-diethylamino-2-ethoxyphenyl)(3-carboxypyridin-2-yl)ketone | 2-phenyl-3-methyl-6-ethylindolizine | Blue |

TABLE VIII-continued

| Keto Acid | Substrate Reactant B | Color Produced |
|---|---|---|
| (4-diethylamino-2-ethoxyphenyl)(3-carboxypyridin-2-yl)ketone | 2-(p-chlorophenyl)indolizine | Green |
| (4-diethylamino-2-ethoxyphenyl)(3-carboxypyridin-2-yl)ketone | 2-(2-pyridyl)indolizine | Green |
| (1-methyl-1,2,3,4-tetrahydroquinolin-6-yl)-(3-carboxypyridin-2-yl)ketone | 1-methyl-2-phenylindolizine | Green |
| (1-methyl-1,2,3,4-tetrahydroquinolin-6-yl)-(3-carboxypyridin-2-yl)ketone | 2-phenyl-3-methylindolizine | Blue-Green |
| (1-methyl-1,2,3,4-tetrahydroquinolin-6-yl)-(3-carboxypyridin-2-yl)ketone | 1-methyl-2-naphthylindolizine | Green |
| (1-methyl-1,2,3,4-tetrahydroquinolin-6-yl)-(3-carboxypyridin-2-yl)ketone | 1,2-diphenylindolizine | Green |
| (1-methyl-1,2,3,4-tetrahydroquinolin-6-yl)-(3-carboxypyridin-2-yl)ketone | 2,3-dimethylindolizine | Blue |
| (1-methyl-1,2,3,4-tetrahydroquinolin-6-yl)-(3-carboxypyridin-2-yl)ketone | 2-phenyl-5-methylindolizine | Blue-Green |
| (2,3,6,7-tetrahydro-1H,5H-benzo[ij]-quinolizin-9-yl)(3-carboxypyridin-2-yl)ketone | 2-phenylindolizine | Green |
| (2,3,6,7-tetrahydro-1H,5H-benzo[ij]-quinolizin-9-yl)(3-carboxypyridin-2-yl)ketone | 1-methyl-2-(p-methoxyphenyl)indolizine | Green |
| (2,3,6,7-tetrahydro-1H,5H-benzo[ij]-quinolizin-9-yl)(3-carboxypyridin-2-yl)ketone | 2-phenyl-3-methyl-6-ethylindolizine | Green |
| (2,3,6,7-tetrahydro-1H,5H-benzo[ij]-quinolizin-9-yl)(3-carboxypyridin-2-yl)ketone | 2-(p-chlorophenyl)indolizine | Green |
| (2,3,6,7-tetrahydro-1H,5H-benzo[ij]-quinolizin-9-yl)(3-carboxypyridin-2-yl)ketone | 2-(2,5-dimethoxyphenyl)indolizine | Green |
| (2,3,6,7-tetrahydro-1H,5H-benzo[ij]-quinolizin-9-yl)(3-carboxypyridin-2-yl)ketone | 2-(p-methoxyphenyl)indolizine | Green |

EXAMPLE 36

Preparation of 3-(1-ethyl-2-methylindol-3-yl)-3-(1-methyl-2-phenylindolizin-3-yl)-1,3-dihydrofuran[3,4-b]quinolin-1-one A mixture of 3.4 grams of (1-ethyl-2-methylindol-3-yl)(3-carboxyquinolin-2-yl)ketone, 2.1 grams of 1-methyl-2-phenylindolizine and 10 ml. of acetic anhydride was heated at 40° C. for 118 minutes and poured into a mixture of ice, toluene and ammonia. The toluene portion was separated, concentrated to about 150 ml., treated with charcoal and filtered. Enough petroleum ether was added to make one liter and a red dye impurity was filtered off. The next day, crystalline material was filtered and recrystallized from a toluene-petroleum ether mixture yielding a product with a melting point of 198°–199° C. A solution of the product in chloroform when applied to record sheet material coated with a zinc-modified phenolic resin produced a blue color.

Additional experiments were performed where a keto-acid and a substrate reactant B were mixed with acetic anhydride and heated. The reaction mixture was cooled, treated with dilute ammonium hydroxide and extracted with toluene. In Table IX is a listing of the reaction pairs and the respective color produced when the toluene extract of the reaction product was applied to a record sheet material coated with a zinc-modified phenolic resin.

TABLE IX

| Keto Acid | Substrate Reactant B | Color Produced |
|---|---|---|
| (1-ethyl-2-methylindol-3-yl)(3-carboxyquinolin-2-yl)ketone | 2-phenylindolizine | Blue |
| (1-ethyl-2-methylindol-3-yl)(3-carboxyquinolin-2-yl)ketone | 2-phenyl-3-methylindolizine | Blue |
| (1-ethyl-2-methylindol-3-yl)(3-carboxyquinolin-2-yl)ketone | 1-methyl-2-naphthylindolizine | Blue |
| (1-ethyl-2-methylindol-3-yl)(3-carboxyquinolin-2-yl)ketone | 1,2-dimethylindolizine | Blue |
| (1-ethyl-2-methylindol-3-yl)(3-carboxyquinolin-2-yl)ketone | 2-phenyl-5-methylindolizine | Blue |
| (1-ethyl-2-methylindol-3-yl)(3-carboxyquinolin-2-yl)ketone | 2-methyl-3-phenylindolizine | Blue |

EXAMPLE 37

Preparation of 3-(4-diethylamino-2-ethoxyphenyl)-3-(1,2-diphenylindolizin-3-yl)-1,3-dihydrofuro[3,4-b]quinolin-1-one A mixture of 2.0 grams of (4-diethylamino-2-ethoxyphenyl)(3-carboxyquinol-2-yl)ketone, 1.4 grams of 1,2-diphenylindolizine and 10 ml. of acetic anhydride was stirred at room temperature for an hour. The mixture was scratched, the resultant precipitate was filtered off and 2.6 grams of product were collected. The product was repeatedly recrystallized to a constant melting point of 265°–266° C. A solution of the product applied to a record sheet material coated with a zinc-modified phenolic resin produced a green color.

Additional experiments were performed where a keto-acid and a substrate reactant B were mixed with acetic anhydride and heated. The reaction mixture was cooled, treated with dilute ammonium hydroxide and extracted with toluene. In Table X is a listing of the reactant pairs and the respective color produced when the toluene extract of the reaction product was applied

TABLE X

| Keto Acid | Substrate Reactant B | Color Produced |
| --- | --- | --- |
| (4-diethylamino-2-ethoxyphenyl)(3-carboxyquinolin-2-yl)ketone | 2-phenylindolizine | Green |
| (4-diethylamino-2-ethoxyphenyl)(3-carboxyquinolin-2-yl)ketone | 1-methyl-2-phenylindolizine | Green |
| (4-diethylamino-2-ethoxyphenyl)(3-carboxyquinolin-2-yl)ketone | 2-phenyl-3-methylindolizine | Blue |
| (4-diethylamino-2-ethoxyphenyl)(3-carboxyquinolin-2-yl)ketone | 1-methyl-2-naphthylindolizine | Green |
| (4-diethylamino-2-ethoxyphenyl)(3-carboxyquinolin-2-yl)ketone | 2,3-dimethylindolizine | Blue |
| (4-diethylamino-2-ethoxyphenyl)(3-carboxyquinolin-2-yl)ketone | 2-phenyl-3-methyl-6-ethylindolizine | Blue |
| (4-diethylamino-2-ethoxyphenyl)(3-carboxyquinolin-2-yl)ketone | 2-(p-chlorophenyl)indolizine | Green |
| (4-diethylamino-2-ethoxyphenyl)(3-carboxyquinolin-2-yl)ketone | 2-(p-methoxyphenyl)indolizine | Green |

EXAMPLE 38

Preparation of 7-(2-phenyl-3-methyl-6-ethylindolizin-1-yl)-7-(1-ethyl-2-methylindol-3-yl)-5,7-dihydrofuro[3,4-b]pyrazin-5-one A mixture of 3.1 grams of (1-ethyl-2-methylindol-3-yl)(2-carboxypyrazin-3-yl)ketone, 2.4 grams of 2-phenyl-3-methyl-6-ethylindolizine and 25 ml. of acetic anhydride was stirred at room temperature for about 1½ hours. The reaction mixture was poured into a mixture of ice and toluene and the mixture was made basic by the addition of cold ammonium hydroxide. The toluene portion was separated, dried with phase separation paper, concentrated, diluted with petroleum ether and chromatographed on alumina. The impurities were eluted with toluene and ethyl acetate. The portion of the alumina column containing the product was removed and the product was eluted from the alumina with methanol. The methanol was evaporated, the resulting solid was dissolved in toluene and petroleum ether was added. After standing several days the solution was filtered and the filtrate evaporated to a yield 0.1 gram of product. A solution of the product when applied to silica gel or a record sheet material coated with a zinc-modified phenolic resin or silton clay produced a blue color.

Additional experiments were performed where a keto acid and a substrate reactant B were mixed with acetic anhydride and heated. The reaction mixture was cooled, treated with dilute ammonium hydroxide and extracted with toluene. In Table XI is a listing of the reactant pairs and the respective color produced when the toluene extract of the reaction product was applied to a record sheet material coated with a zinc-modified phenolic resin.

TABLE XI

| Keto Acid | Substrate Reactant B | Color Produced |
| --- | --- | --- |
| (1-ethyl-2-methylindol-3-yl)(2-carboxypyrazin-3-yl)ketone | 2-phenylindolizine | Blue |
| (1-ethyl-2-methylindol-3-yl)(2-carboxypyrazin-3-yl)ketone | 1-methyl-2-phenylindolizine | Blue |
| (1-ethyl-2-methylindol-3-yl)(2-carboxypyrazin-3-yl)ketone | 2-phenyl-3-methylindolizine | Blue |
| (1-ethyl-2-methylindol-3-yl)(2-carboxypyrazin-3-yl)ketone | 1-methyl-2-naphthylindolizine | Blue-Green |
| (1-ethyl-2-methylindol-3-yl)(2-carboxypyrazin-3-yl)ketone | 1,2-diphenylindolizine | Blue |
| (1-ethyl-2-methylindol-3-yl)(2-carboxypyrazin-3-yl)ketone | 2-methyl-3-phenylindolizine | Blue |

EXAMPLE 39

Preparation of 1-(1-ethyl-2-methylindol-3-yl)-1-(2-phenyl-3-methylindolizin-1-yl)1,3-dihydrofuro[3,4-b]quinoxalin-3-one A mixture of 3.6 grams of (1-ethyl-2-methylindol-3-yl)(3-carboxyquinoxalin-2-yl)ketone, 2.0 grams of 2-phenyl-3-methylindolizine and 10 ml. of acetic anhydride was heated at 35°–36° C. for 45 minutes. The reaction mixture was poured into a mixture of ice, ammonia and toluene. The toluene portion was separated and concentrated yielding 0.9 grams of material which was recrystallized twice from toluene-petroleum ether. The final product had a melting point of 188°–189° C. A solution of the product when applied to a record sheet material coated with a zinc-modified phenolic resin produced a blue color.

Additional experiments were performed where a keto-acid and a substrate reactant B were mixed with acetic anhydride and heated. The reaction mixture was cooled, treated with dilute ammonium hydroxide and extracted with toluene. In Table XII is a listing of the reactant pairs and the respective color produced when the toluene extract of the reaction product was applied to a record sheet material coated with a zinc-modified phenolic resin.

TABLE XII

| Keto Acid | Substrate Reactant B | Color Produced |
| --- | --- | --- |
| (1-ethyl-2-methylindol-3-yl)(3-carboxyquin- | | |

TABLE XII-continued

| Keto Acid | Substrate Reactant B | Color Produced |
|---|---|---|
| (oxalin-2-yl)ketone | 2-phenylindolizine | Blue |
| (1-ethyl-2-methylindol-3-yl)(3-carboxyquin-oxalin-2-yl)ketone | 1-methyl-2-phenylindolizine | Blue-Black |
| (1-ethyl-2-methylindol-3-yl)(3-carboxyquin-oxalin-2-yl)ketone | 1-methyl-2-naphthylindolizine | Blue-Black |
| (1-ethyl-2-methylindol-3-yl)(3-carboxyquin-oxalin-2-yl)ketone | 1,2-diphenylindolizine | Blue-Black |
| (1-ethyl-2-methylindol-3-yl)(3-carboxyquin-oxalin-2-yl)ketone | 2-methyl-3-phenylindolizine | Purple |
| (4-diethylamino-2-ethoxyphenyl)(3-carboxyquin-oxalin-2-yl)ketone | 1-methyl-2-phenylindolizine | Green |
| (4-diethylamino-2-ethoxyphenyl)(3-carboxyquin-oxalin-2-yl)ketone | 2-phenyl-3-methylindolizine | Green |
| (4-diethylamino-2-ethoxyphenyl)(3-carboxyquin-oxalin-2-yl)ketone | 1-methyl-2-naphthylindolizine | Green |
| (4-diethylamino-2-ethoxyphenyl)(3-carboxyquin-oxalin-2-yl)ketone | 1,2-diphenylindolizine | Green |
| (4-diethylamino-2-ethoxyphenyl)(3-carboxyquin-oxalin-2-yl)ketone | 2,3-dimethylindolizine | Blue-Green |
| (4-diethylamino-2-ethoxyphenyl)(3-carboxyquin-oxalin-2-yl)ketone | 2-phenyl-5-methylindolizine | Blue-Green |
| (4-diethylamino-2-chlorophenyl)(3-carboxyquin-oxalin-2-yl)ketone | 1-methyl-2-phenylindolizine | Green-Black |
| (4-diethylamino-2-chlorophenyl)(3-carboxyquin-oxalin-2-yl)ketone | 2-phenyl-3-methylindolizine | Blue |
| (4-diethylamino-2-chlorophenyl)(3-carboxyquin-oxalin-2-yl)ketone | 1,2-diphenylindolizine | Green |
| (4-diethylamino-2-chlorophenyl)(3-carboxyquin-oxalin-2-yl)ketone | 2,3-dimethylindolizine | Blue-Green |
| (4-diethylamino-2-chlorophenyl)(3-carboxyquin-oxalin-2-yl)ketone | 2-phenyl-3-methyl-6-ethylindolizine | Blue-Black |
| (4-diethylamino-2-chlorophenyl)(3-carboxyquin-oxalin-2-yl)ketone | 2-methyl-3-phenylindolizine | Green |

The chromogenic compound Examples identified in Table XIII were subjected to elemental analysis. The molecular formula, the calculated analysis based on the molecular formula and the results found on analysis are listed in the table.

TABLE XIII

| Ex. | Molecular Formula | Calculated Analysis | | | | | Found on Analysis | | | | |
|---|---|---|---|---|---|---|---|---|---|---|---|
| | | C | H | N | O | Cl | C | H | N | O | Cl |
| 1 | $C_{38}H_{30}N_2O_2$ | 83.23% | 5.72% | 4.94% | | | 83.49% | 5.53% | 5.12% | | |
| 2 | $C_{39}H_{30}N_2O_2$ | 83.83% | 5.41% | 5.01% | | | 83.93% | 5.50% | 4.91% | | |
| 3 | $C_{29}H_{22}N_2Cl_4O_2$ | 60.86% | 3.88% | 4.90% | | 24.78% | 60.93% | 3.92% | 4.83% | | 24.80% |
| 14 | $C_{29}H_{30}N_2O_3$ | 76.63% | 6.65% | 6.16% | | | 76.84% | 6.66% | 6.05% | | |
| 15 | $C_{33}H_{31}N_3O_2$ +$C_7H_8$(1 mole toluene) | 80.91% | 6.62% | 7.08% | | | 81.12% | 6.73% | 7.12% | | |
| 16 | $C_{34}H_{32}N_2O_3$ | 79.04% | 6.24% | 5.42% | | | 79.22% | 6.35% | 5.35% | | |
| 23 | $C_{38}H_{29}N_3O_2$ | 81.55% | 5.22% | 7.51% | | | 81.50% | 5.36% | 7.48% | | |
| 24 | $C_{28}H_{25}N_3O_2$ | 77.22% | 5.79% | 9.65% | | | 77.40% | 5.91% | 9.60% | | |
| 25 | $C_{32}H_{25}N_3O_2$ | 79.48% | 5.21% | 8.69% | | | 79.28% | 5.30% | 8.43% | | |
| 30 | $C_{36}H_{37}N_3O_2$ | 73.07% | 6.30% | 7.10% | | 13.52% | 73.18% | 6.47% | 6.82% | | 13.45% |
| 36 | $C_{36}H_{29}N_3O_2$ | 80.72% | 5.46% | 7.84% | | | 80.87% | 5.48% | 7.63% | | |
| 39 | $C_{36}H_{28}N_4O_2$ | 78.81% | 5.14% | 10.21% | | | 78.60% | 5.27% | 10.31% | | |

Preparation of Pressure Sensitive Copy Paper

Solutions of three chromogenic compounds of the present invention were individually microencapsulated according to U.S. Pat. No. 4,100,103. The microcapsules were mixed with additives, and the mixture was coated and dried to produce a pressure sensitive transfer sheet.

EXAMPLE 40

A 1.7% solution of the chromogenic compound of Example 4 in a 64:36 weight ratio solvent mixture of ethyldiphenylmethane (U.S. Pat. No. 3,996,405) and saturated hydrocarbon oil (distillation range: 370°–500° F.) was prepared. A solution was made of a mixture of 50 grams of a 10% water solution of EMA-31 [poly-(ethylene-co-maleic anhydride), sold by Monsanto Company] and 100 fgrams of water, the pH of the solution was adjusted to 4 with 20% sodium hydroxide and 25 grams of Resimene 714 (an 80% solution of methylated methylol melamine in water sold by Monsanto Company) was added. Into this aqueous solution was emulsified the above chromogenic compound solution to an oil drop size of predominantly less than 10 microns. This emulsion was placed with stirring in a 55° C. water bath. After at least 30 minutes, heating of the bath was discontinued and the microcapsule batch continued to stir in the cooling bath overnight.

The following mixture was prepared, dispersed in a blender, coated on a paper substrate with a #12 wire-wound coating rod and dried:

100 grams of above microcapsule slurry
120 grams of water
10 grams of uncooked wheat starch 40 grams of 10%
Penford Gum 230 (modified corn starch binder)

EXAMPLE 41

In a similar manner to Example 40, a 1.7% solution of the chromogenic compound of Example 25 was encapsulated and the microcapsules coated to produce a pressure sensitive transfer sheet.

EXAMPLE 42

In a similar manner to Example 40, a 1.7% solution of the chromogenic compound of Example 25 was encapsulated and the microcapsules coated to produce a pressure sensitive transfer sheet.

The three pressure sensitive transfer sheets (CB sheets) of Examples 40, 41 and 42 were tested face to face with underlying receiving sheets (CF sheets), each bearing a coating comprising an oil-soluble metal salt of a phenol-formaldehyde novolak resin made by procedures described in U.S. Pat. Nos. 3,732,120 and 3,455,721 (CF 1), silton clay (CF 2), or a metal salt of an aromatic carboxylic acid described in U.S. Pat. No. 4,022,936 (CF 3). These CB-CF couplets were then subjected to a calender intensity (CI)test.

A CI test is essentially a rolling pressure test and is conducted to determine the amount of color developed from the transfer of marking liquid obtained by such rolling pressure. The results are reported as the ratio of the reflectance of the marks produced on the CF sheet as compared to the background reflectance of the CF paper ($I/I_o$) expressed as a percentage. In the CI test the lower the value, the more intense the mark.

The CI results listed in Table XIV were obtained from the indicated CB-CF pairs:

TABLE XIV

| CB Sheets | Calender Intensity (I/Io %) | | |
|---|---|---|---|
|  | CF 1 | CF 2 | CF 3 |
| Ex. 40 | 56 | 59 | 48 |
| Ex. 41 | 64 | 61 | 69 |
| Ex. 42 | 61 | 56 | 62 |

EXAMPLE 43

Preparation of 3-(4-dimethylaminophenyl)-3-(1-methyl-2-phenylindolizin-3-yl)naphthalide A mixture of 3.2 grams of 8-(p-dimethylaminobenzoyl)-1-naphthoic acid, 2.1 grams of 2-phenyl-1-methylinodolizine and 25 ml. of acetic anhydride was stirred at 94° C. for 24 minutes. The reaction mixture was cooled and poured into a mixture of ice, ammonia and toluene. The toluene was dried by means of phase separating paper. The solution was concentrated and diluted with petroleum ether. Filtering yielded 3.3 grams of product which was recrystallized to a constant melting point of 171°-171.5° C.

A solution of the product when applied to a record sheet material coated with a zinc-modified phenolic resin produced a green color, and when applied to a record sheet material coated with silton clay produced a blue color.

EXAMPLES 44–47

According to substantially the same procedure as described in Example 43, 8-(p-dimethylaminobenzoyl)-1-naphthoic acid was reacted with a substantially equimolar amount of substrate reactant B in the presence of acetic anhydride with heating. The reaction product was separated and recrystallized to a constant melting point. A solution of each product was used to produce a color on record sheet material coated with a zinc-modified phenolic resin and on record sheet material coated with silton clay. These reactants and the results obtained are listed in Table XV.

TABLE XV

| Example | Substrate Reactant B | Melting Point | Color on Record Sheet Material Coated with | |
|---|---|---|---|---|
|  |  |  | zinc-modified phenolic resin | Silton Clay |
| 44 | 1,2-diphenyl-indolizine | 217–218° C. | green | green |
| 45 | 2-phenyl-3-methyl-indolizine | 225–226° C. | green | blue |
| 46 | 2-phenyl-4-methyl-indolizine | 283.5–239° C. | green | neutral |
| 47 | 2-phenyl-indolizine | 197.5–198.5° C. | green | blue |

Preparation of 1-Carboethoxy-2-phenylindolizine

A solution of 14.86 grams (0.090 mole) of ethyl-2-pyridine acetate and 8.96 grams (0.045 mole) of α-bromoacetophenone in 40 ml of acetone was refluxed seven hours. The solvent was removed under reduced pressure and 40 ml or 2 N HCl added.

After standing for several hours diethylether (200 ml) was added. The mixture was filtered to yield 5.83 grams of desired product, m.p. 101°–103° C.

The ether layer was separated from the filtrate and evaporated to a volume of 25 ml. From this was obtained an additional 3.80 grams of desired product, m.p. 101°–103° C. Total yield, 80.7%.

EXAMPLE 48

Preparation of 7-(1-ethyl-2-methylindol-3-yl)-7-(1-carboethoxy-2-phenylindolizin-3-yl)-5,7-dihydrofuro[3,4-b]pyridin-5-one A solution of 1.23 grams (0.004 mole) of (1-ethyl-2-methylindol-3-yl) (3-carboxypyridin-2-yl)ketone and 1.06 grams (0.004 mole) of 1-carboethoxy-2-phenylindolizine in 10 ml. of acetic anhydride was heated 1.5 hours at 60° C.

The solution was poured into 150 ml. of water and slowly brought to pH 7.0 with 20% sodium hydroxide solution. To minimize hydrolysis of the ester the final pH adjustment was made with dilute sodium bicarbonate solution.

The isolated solid was dissolved in toluene and treated with activated carbon and a little $Al_2O_3$. The toluene solution was evaporated under reduced pressure to leave 1.79 grams (80%) of desired product. On TLC (silica) there was developed an overwhelming amount of major blue isomer and a smaller amount of slower moving blue isomer.

An aliquot was chromatographed on a small alumina column to give nearly white product, m.p. 169°–171° C. This was exclusively the major isomer.

EXAMPLE 49

Preparation of 3-(1-ethyl-2-methylindol-3-yl)-3-(1-carboethoxy-2-phenylindolizin-3-yl)phthalide A solution of 1.78 grams (0.0058 mole) of (1-ethyl-2-methylindol-3-yl) (2-carboxyphenyl)ketone and 1.54 grams (0.0058 mole) of 1-carboethoxy-2-phenylindolizine in 20 ml. of acetic anhydride was heated 2.5 hours at 60° C.

A solution was dropped into 250 ml. of water containing 17.5 grams of sodium hydroxide. After 2 hours stirring at room temperature the resulting slightly amber solid was filtered to give 3.11 grams. TLC (silica) showed a good quantity of fast moving blue, some slower red and a small amount of second blue isomer.

The product was chromatographed on a short rapid flow silica gel column (50 grams) using 5% acetone-toluene eluent. There was obtained 2.65 grams (80.5%) of light tan solid. TLC showed fast moving blue and a trace of slower red.

An aliquot was rechromatographed to give a purified sample, m.p. 157°–159° C.

EXAMPLE 50

Preparation of 7-(4-diethylamino-2-ethoxyphenyl)-7-(1-carboethoxy-2-phenylindolizin-3-yl)-5,7-dihydrofuro[3,4-b]pyridin-5-one A solution of 1.03 grams (0.003 mole) of (4-diethylamino-2-ethoxyphenyl) (3-carboxypyridin-2-yl)ketone and 0.80 grams (0.003 mole) of 1-carboethoxy-2-phenylindolizine in 15 ml. of acetic anhydride was heated at 60° C. for 2 hours.

The solution was poured into 150 ml. of water and slowly brought to pH 7.0 with dilute sodium hydroxide. Additional dilute sodium bicarbonate solution was added and the mixture stirred 2 hours.

The product was extracted into toluene, treated with activated carbon and evaporated under reduced pressure. There was obtained 1.63 grams (92.6%) of light grey powder. TLC showed an overwhelming amount of fast moving green spot and a small amount of slower green spot.

A 0.153 gram aliquot was recrystallized from ethanol to give 0.130 gram of white product, m.p. 218°–219° C.

EXAMPLE 51

Preparation of 3-(4-diethylamino-2-ethoxyphenyl)-3-(1-carboethoxy-2-phenylindolizin-3-yl)phthalide A solution of 1.36 grams (0.004 mole) of (4-diethylamino-2-ethoxyphenyl) (3-carboxypyridin-2-yl)ketone and 1.06 grams (0.004 mole) of 1-carboethoxy-2-phenylindolizine in 10 ml. of acetic anhydride was heated 2 hours at 55°–60° C. Crystallization began in the cooled solution.

The mixture was poured into water and slowly brought to pH 9.0 with dilute sodium hydroxide solution. After 2 hours stirring at room temperature the solid was filtered and finally a 10 ml. mixture of 50% acetone-water was added. There was obtained 2.2 grams of light tan solid, m.p. 172°–175° C. This was further pulverized and washed on a filter with 5 ml. of acetone. There remained 1.70 grams (72.6%) of light cream colored solid, m.p. 186.5°–188.0° C.

TLC (silica) showed almost exclusively one faster moving green isomer and a very small amount of second isomer.

EXAMPLE 52

Preparation of Bis-7,7-(1-carboethoxy-2-phenylindolizin-3-yl)-5,7-dihydrofuro[3,4-b]pyridin-5-one A mixture of 0.15 gram (0.001 mole) of quinolinic anhydride, 0.53 gram (0.002 mole) of 1-carboethoxy-2-phenylindolizine and 10 ml. of acetic anhydride was heated at 75° C. The materials slowly went into solution and a green color developed. After 2 hours a substantial amount of the indolizine was still unreacted. The temperature was raised to 85° C. for an additional 2 hours. TLC on an aliquot showed increased product spots and reduced starting indolizine. The reaction was continued for an additional 16 hours at 60° C.

The solution was poured into 100 ml. of water and slowly brought to pH 8.5 with dilute sodium hydroxide solution. The somewhat sticky mass was extracted into toluene. Evaporation of the toluene layer left 0.46 gram. TLC (silica) of this showed a small amount of unreacted indolizine, a faster moving green and a lower moving green.

The material was chromatographed on 10 grams of Silica gel. A center cut was made to give 0.17 gram of solid product. This still contains a mixture of the isomers.

A toluene solution of each product of examples 43–47 was used to produce a color on record sheet material coated with a zinc-modified phenolic resin an on record sheet material coated with silton clay. These reactants and the results obtained are listed on Table XVI.

TABLE XVI

| Example No. | Color on Record Sheet Material Coated With | |
|---|---|---|
| | zinc-modified phenolic resin | silton clay |
| 48 | blue | blue |
| 49 | blue | blue |
| 50 | green | green |
| 51 | green | green |
| 52 | green | green |

The invention being thus described, it will be obvious that the same may be varied in many ways. Such variations are not to be regarded as a departure from the spirit and scope of the invention, and all such modifications are intended to be included within the scope of the following claims.

What is claimed is:

1. A compound represented by the formula:

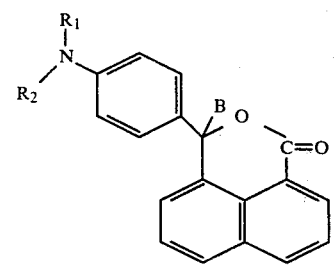

wherein B is:

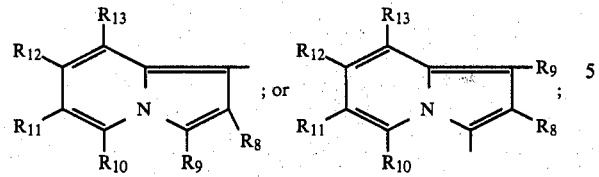

$R_1$ and $R_2$ are: hydrogen or alkyl of one to four carbon atoms, $R_8$ is: phenyl, phenyl which is substituted by methoxy, phenyl, chloro or dimethylamino or alkyl of one to four carbon atoms, $R_9$ is: hydrogen, alkyl of one to four carbon atoms or phenyl; and $R_{10}$, $R_{11}$, $R_{12}$ and $R_{13}$ are: hydrogen or alkyl of one to four carbon atoms.

2. The compound of claim 1 wherein $R_1$ and $R_2$ are alkyl of one to four carbon atoms.

3. The compound of claim 2 wherein $R_8$ is phenyl.

4. The compound of claim 3 wherein $R_1$ and $R_2$ are methyl.

5. The compound of claim 4 wherein B is

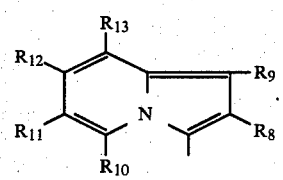

6. The compound of claim 5 wherein $R_{10}$, $R_{11}$, $R_{12}$ and $R_{13}$ are hydrogen.

7. The compound of claim 6 wherein $R_9$ is hydrogen.

8. The compound of claim 6 wherein $R_9$ is methyl.

9. The compound of claim 6 wherein $R_9$ is phenyl.

10. The compound of claim 4 wherein B is

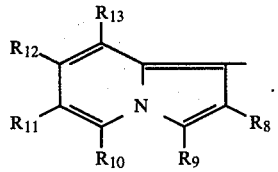

11. The compound of claim 10 wherein $R_{10}$, $R_{11}$, $R_{12}$ and $R_{13}$ are hydrogen.

12. The compound of claim 11 wherein $R_9$ is methyl.

13. The compound of claim 10 wherein:
$R_{10}$ is methyl; and
$R_{11}$, $R_{12}$ and $R_{13}$ are hydrogen.

14. The compound of claim 13 wherein $R_9$ is hydrogen.

15. A compound represented by the formula:

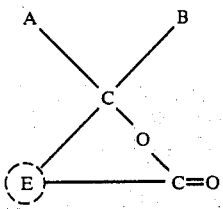

wherein E is:

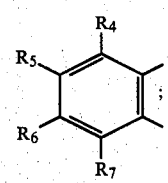

$R_4$, $R_5$, $R_6$ and $R_7$ are: hydrogen, chlorine or dialkylamino wherein alkyl is alkyl of one to four carbon atoms;

A is

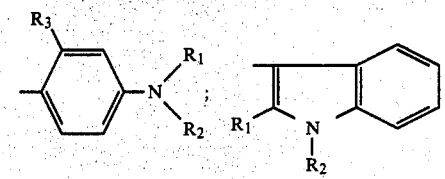

or B;
$R_1$ and $R_2$ are: hydrogen or alkyl of one to four carbon atoms;
$R_3$ is: hydrogen or alkoxy of one to four carbon atoms;
B is:

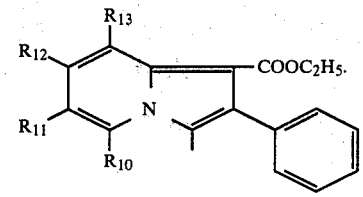

; and
$R_{10}$, $R_{11}$, $R_{12}$ and $R_{13}$ are: hydrogen or alkyl.

16. The compound of claim 15 wherein $R_4$, $R_5$, $R_6$, $R_7$, $R_{10}$, $R_{11}$, $R_{12}$ and $R_{13}$ are hydrogen.

17. The compound of claim 16 wherein A is

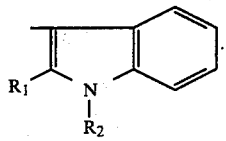

18. The compound of claim 17 wherein:
$R_1$ is methyl; and
$R_2$ is ethyl.

19. The compound of claim 16 wherein A is

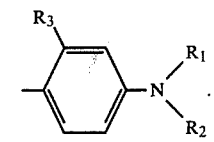

20. The compound of claim 19 wherein:
$R_1$ and $R_2$ are ethyl; and
$R_3$ is ethoxy.

* * * * *